(12) United States Patent
Boesen (10) Patent No.: US 6,470,893 B1
(45) Date of Patent: Oct. 29, 2002

(54) WIRELESS BIOPOTENTIAL SENSING DEVICE AND METHOD WITH CAPABILITY OF SHORT-RANGE RADIO FREQUENCY TRANSMISSION AND RECEPTION

(76) Inventor: Peter V. Boesen, 4026 Beaver Ave., Des Moines, IA (US) 50310

( * ) Notice: Subject to any disclaimer, the term of this patent is extended or adjusted under 35 U.S.C. 154(b) by 0 days.

(21) Appl. No.: 09/570,758

(22) Filed: May 15, 2000

(51) Int. Cl.$^7$ .......................... A61B 19/00; H04L 27/10
(52) U.S. Cl. ...................... 128/899; 128/903; 375/272
(58) Field of Search ................. 600/300, 317, 600/382, 411, 454, 546, 595; 340/870.12, 128, 375

(56) References Cited

U.S. PATENT DOCUMENTS

| | | |
|---|---|---|
| 3,603,881 A | 9/1971 | Thornton |
| 3,815,109 A * | 6/1974 | Carraway et al. ...... 340/870.12 |
| 4,374,382 A | 2/1983 | Markowitz ............. 340/870.01 |
| 4,528,987 A | 7/1985 | Slocum ...................... 128/696 |
| 4,635,646 A | 1/1987 | Gilles et al. ................ 128/696 |
| 4,672,976 A | 6/1987 | Kroll |
| 4,742,831 A | 5/1988 | Silvian ........................ 128/710 |
| 4,773,427 A | 9/1988 | Inoue et al. ................ 128/696 |
| 4,777,961 A | 10/1988 | Saltzman |
| 4,791,933 A | 12/1988 | Asai et al. .................. 128/640 |
| 4,792,145 A | 12/1988 | Eisenberg et al. |
| 4,947,859 A | 8/1990 | Brewer et al. |
| 5,010,890 A | 4/1991 | Pfohl et al. |
| 5,035,247 A | 7/1991 | Heimann |
| 5,052,398 A | 10/1991 | Gober ........................ 128/696 |
| 5,365,937 A | 11/1994 | Reeves et al. |
| 5,381,798 A | 1/1995 | Burrows ..................... 128/696 |
| 5,417,222 A | 5/1995 | Dempsey et al. ........... 128/696 |
| 5,436,564 A * | 7/1995 | Kreger et al. ................ 600/411 |
| 5,458,123 A | 10/1995 | Unger ......................... 128/696 |
| 5,492,129 A | 2/1996 | Greenberger |
| 5,579,781 A * | 12/1996 | Cooke ......................... 600/546 |
| 5,634,468 A | 6/1997 | Platt et al. ................... 128/696 |
| 5,660,177 A * | 8/1997 | Faupel et al. ............... 600/382 |
| 5,721,783 A | 2/1998 | Anderson |
| 5,766,208 A * | 6/1998 | McEwan ..................... 600/595 |
| 5,807,258 A * | 9/1998 | Cimochowski et al. ..... 600/454 |
| 5,833,603 A * | 11/1998 | Kovacs et al. .............. 600/317 |
| 6,002,777 A | 12/1999 | Grasfield et al. |
| 6,099,486 A | 8/2000 | Fruscello |

FOREIGN PATENT DOCUMENTS

GB     2 074 817 A     11/1981

OTHER PUBLICATIONS

Article entitled, "A new level of Control for Faster, More Predictable Recovery," by Medical Aspect, as early as 1997.

* cited by examiner

Primary Examiner—Kevin Shaver
Assistant Examiner—Nikita R Veniaminov
(74) Attorney, Agent, or Firm—McKee, Voorhees & Sease, P.L.C.

(57) ABSTRACT

Devices and methods which sense a biopotential are disclosed. The sensed biopotential is used to modulate an output signal. The power of the output signal is limited so that the signal will attenuate within a predetermined distance. In one embodiment, a wireless ECG electrode has a transmitter in communication with the electrode. The transmitter outputs a signal which is modulated by the output of the electrode. The power of the signal is limited so that the signal will attenuate within a predetermined distance from a transmission point.

26 Claims, 6 Drawing Sheets

WIRELESS BIOPOTENTIAL SENSING DEVICE AND METHOD WITH CAPABILITY OF SHORT-RANGE RADIO FREQUENCY TRANSMISSION AND RECEPTION

BACKGROUND OF THE INVENTION

A. Field of the Invention

The present invention relates to devices and methods for monitoring biopotentials. More particularly, but without limitation, the present invention relates to a method and device for monitoring or sensing a biopotential and wirelessly transmitting the monitored condition within a predetermined distance.

B. Problems in the Art

Biopotential sensors are known in the art. In a conventional arrangement, such as with electrocardiograph (ECG) leads, the sensors/leads are connected to a monitor or display through wires. The use of wire connections can create problems.

For example, there are times when a patient to whom ECG leads are attached will need to be moved very quickly to a remote part of the hospital. In this scenario, the electrodes must either be removed from the patient or the ECG monitor must also be moved with the patient. Removing the electrodes from the patient requires additional time which is undesirable when the patient is facing a situation that must be acted on quickly. If the leads are left on the patient, then the ECG monitor must be moved with the patient, also requiring additional time and/or personnel to aide in moving the monitor. Also, the wires between the leads and the monitor can create further hazards to the patient and the equipment.

In addition to creating problems when a patient is being moved, wire connections can also cause problems when a patient is stationary. For example, hospital personnel can accidentally trip over a wire or the patient could accidentally jerk one of the leads free from the monitor. If the disconnection of the electrode from the monitor is not detected and acted upon, a patient could conceivably suffer needless deleterious consequences. There is a need in the art for a biopotential sensing device and method which minimizes the use of wire connections.

In an attempt to solve some of these problems, wireless ECGs have been invented. However, with an increase in the use of wireless ECGs and other wireless communication devices, the probability of electromagnetic interference increases. In addition, in an attempt to control health care costs, there has been an increase in the number of hospital rooms where more than one patient occupies a given room. This makes the probability of electromagnetic interference even greater. In these situations, it is desirable that there be no cross-linkage, or electromagnetic interference, between monitoring devices of two patients in close physical proximity. None of the known wireless ECGs have attempted to solve the problem of electromagnetic interference between analogous devices, monitoring different patients, through limitation of the power of the output signal.

While the problem of electromagnetic interference is of particular concern in the hospital setting, there are other situations in which interference can be problematic. Given the increase in the number of wireless communication devices that are used within a home (e.g., cell phones, remote controls) there is a need in the art for a method and device which allows for the use of multiple wireless communication devices while also limiting electromagnetic interference. It will be apparent to those skilled in the art that the teachings of this specification can be applied outside of the medical context.

Therefore, it is a primary object of the present invention to provide a wireless biopotential sensing device and method which solves problems and deficiencies in the art.

It is a further object of the present invention to provide a method and device which senses biopotentials and transmits the sensed biopotential using an ultra short range radio frequency.

It is a further object of the present invention to provide a biopotential sensor and transmitter combination which outputs signals that do not interfere with similar devices.

It is a further object of the present invention to minimize multipath interference.

It is a further object of the present invention to provide an output signal which maintains a patient's privacy.

It is a further object of the present invention to provide a wireless biopotential sensor and transmitter which minimizes battery discharge.

It is a further object of the invention to provide a biopotential sensing system and method which is capable of two-way communications between an electrode and a remote transceiver.

These, as well as objects and features of the present invention, will be apparent from the following detailed description and claims in conjunction with the accompanying drawings.

SUMMARY OF THE INVENTION

The present invention includes a new biopotential monitoring system which has the advantages of limiting electromagnetic interference while consuming low power. The biopotential monitoring system includes a biopotential sensor. The biopotential monitoring system also includes a transmitter which is in operative communication with the sensor. The transmitter is adapted to broadcast a first signal which is modulated by a sensed biopotential. The transmitter is further adapted to limit the power of the first signal so that the signal attenuates within a predetermined distance from the transmitter.

The biopotential monitoring system may also include a receiver which is adapted to receive the first signal. Optionally, the receiver may be in operative communication with a computer to store or record the received signal. In one embodiment, the biopotential monitoring system can also include a second receiver which can receive signals to instruct the sensor to perform various functions, such as turning the power off, transmitting a signal, or waiting in standby mode.

The present invention can also include a method of monitoring a biopotential signal. A method of monitoring a biopotential signal includes the steps of sensing a biopotential signal with a biopotential sensor, and broadcasting a first signal which is modulated by the sensed biopotential. The method also includes the step of limiting the power of the first signal so that it attenuates within a predetermined distance from the transmitter. The method can optionally include the steps of receiving the broadcast signal at a first receiver and communicating the broadcast signal to a computer where it can be stored and/or analyzed. Further, the method may include additional steps such as transmitting a second signal to a biopotential sensor to facilitate a secondary function.

DETAILED DESCRIPTION OF THE PREFERRED EMBODIMENT

The present invention will be described as it applies to its preferred embodiment. It is not intended that the present invention be limited to the described embodiment. It is intended that the invention cover all modifications and alternatives which may be included within the spirit and scope of the invention.

Figure 1:
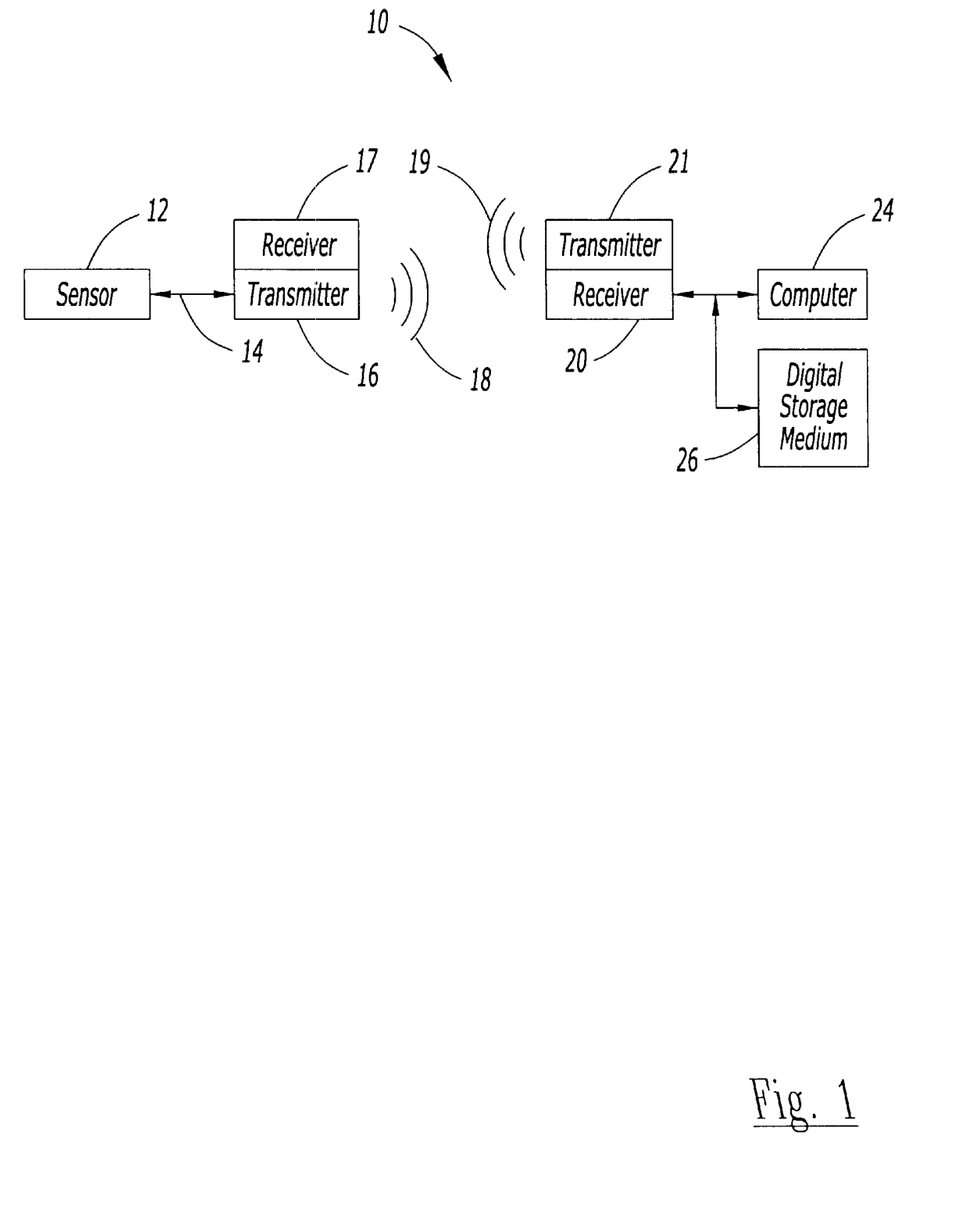
FIG. 1 is a block diagram of an embodiment of a sensing system and method according to the present invention.

FIG. 1 shows a block diagram of a sensing system and method 10 according to an embodiment of the present invention. System 10 includes a sensor 12. Sensor 12 could be any sensor, such as a microphone, a thermistor, a proximity detector, or any other sensor which is capable of generating an electrical output. In the preferred embodiment, the sensor is an ECG electrode. The output 14 of sensor 12 is input into a transmitter 16. Note that arrow 14 is shown as being bi-directional to illustrate two-way communication between sensor 12 and either transmitter 16 or receiver 17.

Transmitter 16 outputs a signal 18 which is modulated by the output 14 of sensor 12. Broadcast signal 18 is preferably a radio frequency (RF) signal. Signal 18 preferably has a frequency of either around 900 MHz or 2.4 GHz, as these two frequencies are still open to the public. Of course, other frequencies could be used. Preferably, broadcast signal 18 is a digital spread spectrum signal. The power of broadcast signal 18 is limited so that the signal will attenuate within a predetermined distance from a transmitter (explained more fully later on).

Receiver 20 is adapted to receive broadcast signal 18. Receiver 20 can also be further adapted to recover the sensed information from broadcast signal 18. Receiver 20 is a conventional receiver.

Receiver 20 may contain an analog-to-digital converter. Receiver 20 may be adapted so that it outputs 22 the sensed information to either a computer 24 or to a digital storage medium 26. The digital information 22 could be used for further analysis by computer 24. Of course, computer 24 could subsequently write the information to digital storage medium 26.

The system 10 may also be configured for two-way communications. A second transmitter 21 may be in operative communication with either the first receiver 20 or the computer 24. The second transmitter 21 can be adapted to output a second signal 19 which is received by the second receiver 17. The second signal 19 may contain instructions from the computer 24, the first receiver 20, or the second transmitter 21. The second receiver 17 is adapted to receive the second signal 19. The second receiver 17 can be in operative communication with the sensor 12 and/or the first transmitter 16. The second signal 19 may contain instructions "telling" the sensor 12 (or first transmitter 16) to perform a certain function, such as turning the power off, or begin transmitting first signal 18.

Figure 2:
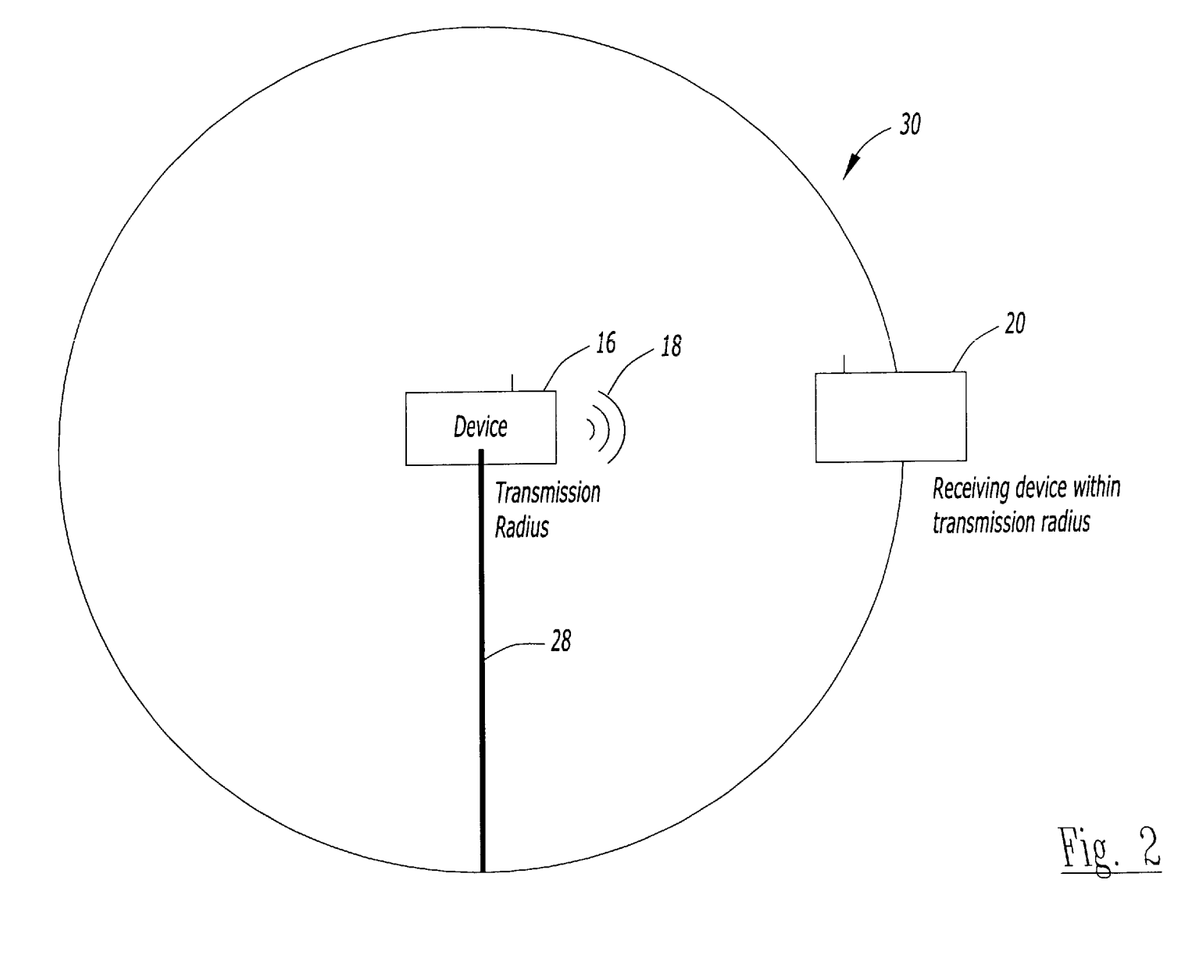
FIG. 2 is a schematic diagram which illustrates the limited range transmission protocol of the present invention.

FIG. 2 shows a schematic diagram of the limited range transmission protocol 30 according to the present invention. Transmitter 16 outputs radio frequency signal 18. Transmitter 16 is adapted such that the output power of signal 18 is limited so that signal 18 will attenuate within the transmission radius 28. As shown in FIG. 2, transmitter 16 outputs an omnidirectional signal 18. Of course, transmitter 16 could be equipped with a directional antenna so that the output signal 18 was only detectable within a predetermined direction. Receiver 20 needs to be located within this transmission radius 28 to receive signal 18. It should be noted that transmitter 16 and receiver 20 could both be transceivers, if two-way communication is needed. Receiver 20 could have a transmitter and broadcast a signal to a receiver which is physically separated from the transmitter 16.

The length of transmission radius 28 will vary depending on the specific application of the protocol. When used in a hospital setting, the transmission radius may be as little as 10 to 12 feet. For other settings, such as for use in the house, the transmission radius may be a greater distance. By limiting the power of output signal 18, transmitter 16 will use less power. If transmitter 16 is battery powered, the battery life will be substantially increased.

Furthermore, the protocol shown in FIG. 2 helps minimize multipath interference. Because signal 18 attenuates within a short distance, receiver 20 will not receive as many "bounced" signals. This helps ensure accuracy of the reception.

In addition, the privacy of the transmitted signal 18 is enhanced. Since signal 18 attenuates within a given range, a monitor or "spying" device would have to be located within the given transmission radius 28 to intercept the signal 18. As the transmission radius 28 is decreased, it is unlikely that a monitoring device could be placed within this area without being noticed.

Limiting the power of signal 18 also reduces radiation exposure since the intensity of the electromagnetic field of signal 18 is reduced. Exposure to high intensity electromagnetic fields has been linked with increased health problems. By limiting the power of the signal 18, these associated health problems will be reduced.

Finally, by limiting the power of signal 18, transmitter 16 will produce less heat, due to the lower power consumption of transmitter 16. This is beneficial when transmitter 16 is attached to a person. It is also beneficial in increasing the reliability of transmitter 16. Since heat is reduced, the failure of the electrical components of transmitter 16 due to heat effects should be reduced.

Figure 3:
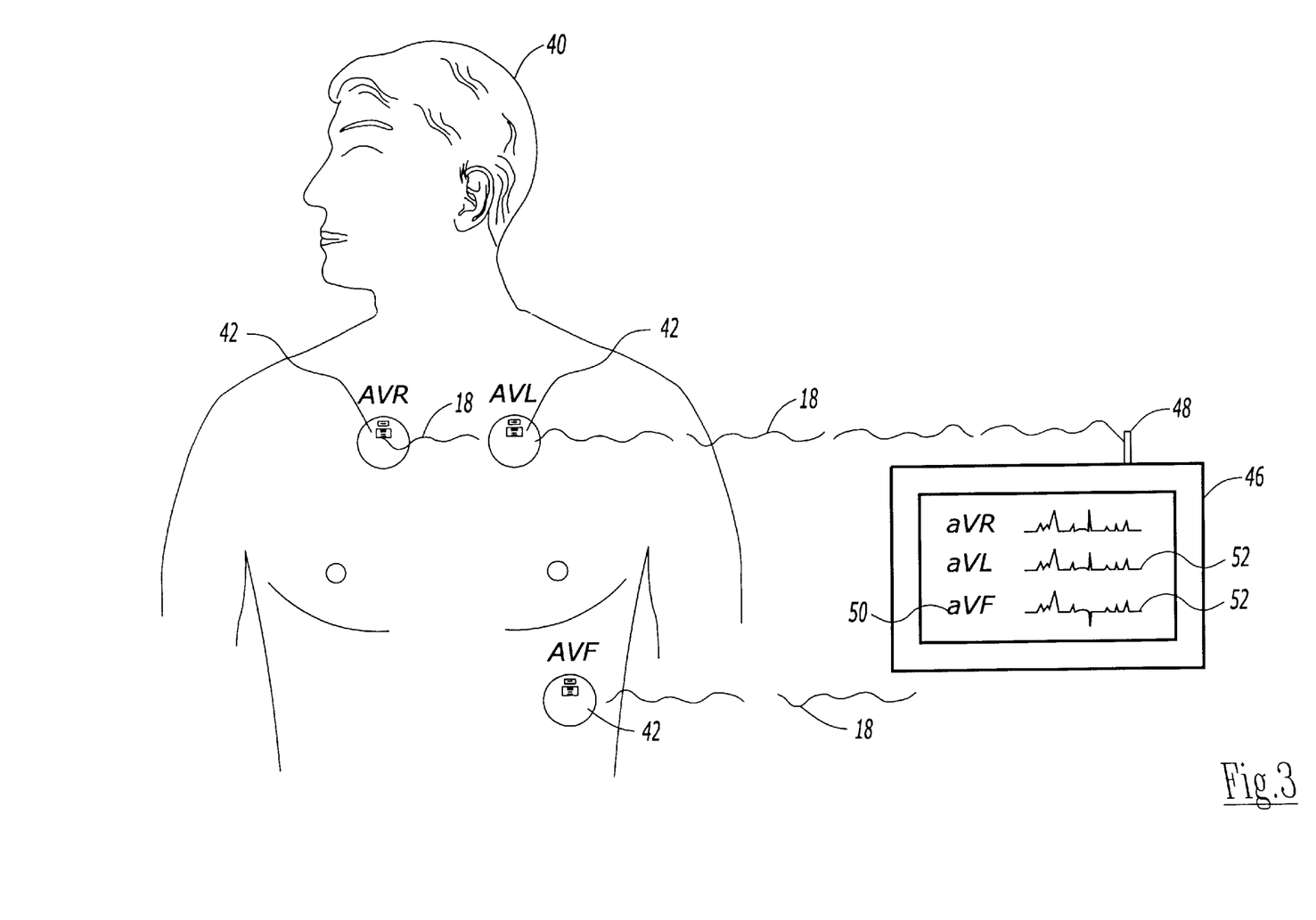
FIG. 3 is a schematic diagram which shows one embodiment of ECG electrodes and transmitters attached to a patient.

FIG. 3 shows a schematic diagram of a patient 40 with ECG electrodes 42 attached to the patient in a conventional manner. Electrode 42 includes a transmitter. Electrodes or transmitter 42 broadcast a signal 18 which is modulated by the sensed electrical activity of the heart. The power of the broadcast signal 18 is limited so that the signal will attenuate within a predetermined distance from the electrode 42 or transmission point (see FIG. 2).

Receiver 46 receives signal 18 through its antenna 48. Receiver 46 also has a display screen 50 which displays the heart waveforms 52 from the electrodes 42. Receiver 46 could be equipped with a plurality of antennas 48 to receive the signals from the various electrodes 42. Rather than a plurality of antennas 48, receiver 46 could have a single antenna and could distinguish between the multiple signals through the use of multiple tuner cards. Of course, it will be apparent to those skilled in the art that there are numerous ways that receiver 46 could be adapted to distinguish between the various signals from the different ECG transmitters 42. It will also be apparent that the output signals 18 from the transmitter 42 could be modulated in a number of ways to distinguish the various signals 18.

Figure 4:
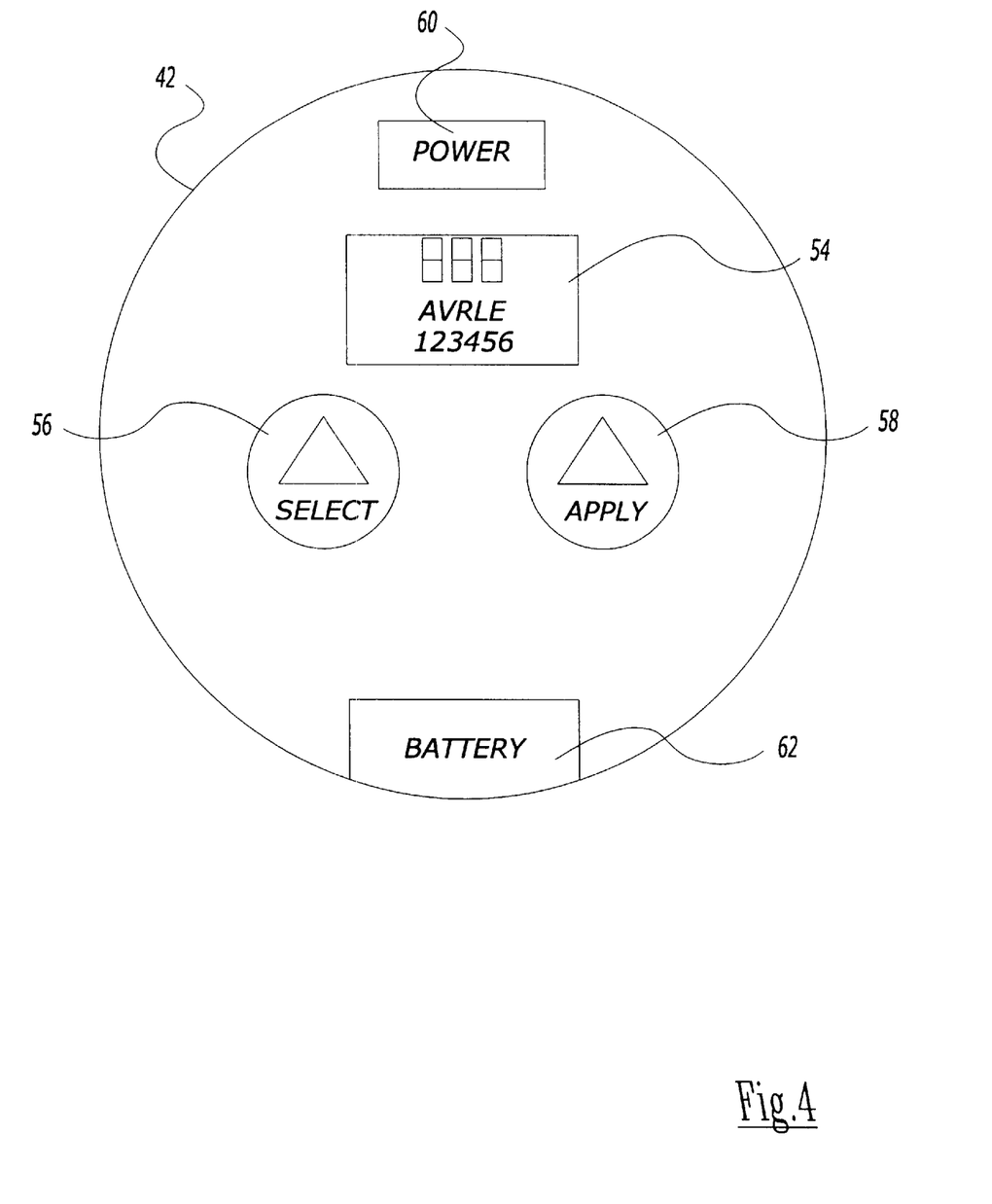
FIG. 4 is a top plan view of one embodiment of an ECG electrode and transmitter according to the present invention.

FIG. 4 shows a top plan view of the wireless electrode 42. Electrode 42 includes a liquid crystal display (LCD) 54. LCD 54 displays information about the electrode, such as where the electrode should be placed (e.g., $AV_R$, $AV_L$) Transmitter 42 also includes a selection button 56 and an apply button 58. The selection button 56 is utilized to define the position of the sensor. The apply button 58 locks in the particular selection.

Electrode 42 is preferably battery powered. Electrode 42 contains a battery hatch 62. The battery hatch 62 is preferably a conventional rechargeable battery hatch.

Figure 5:
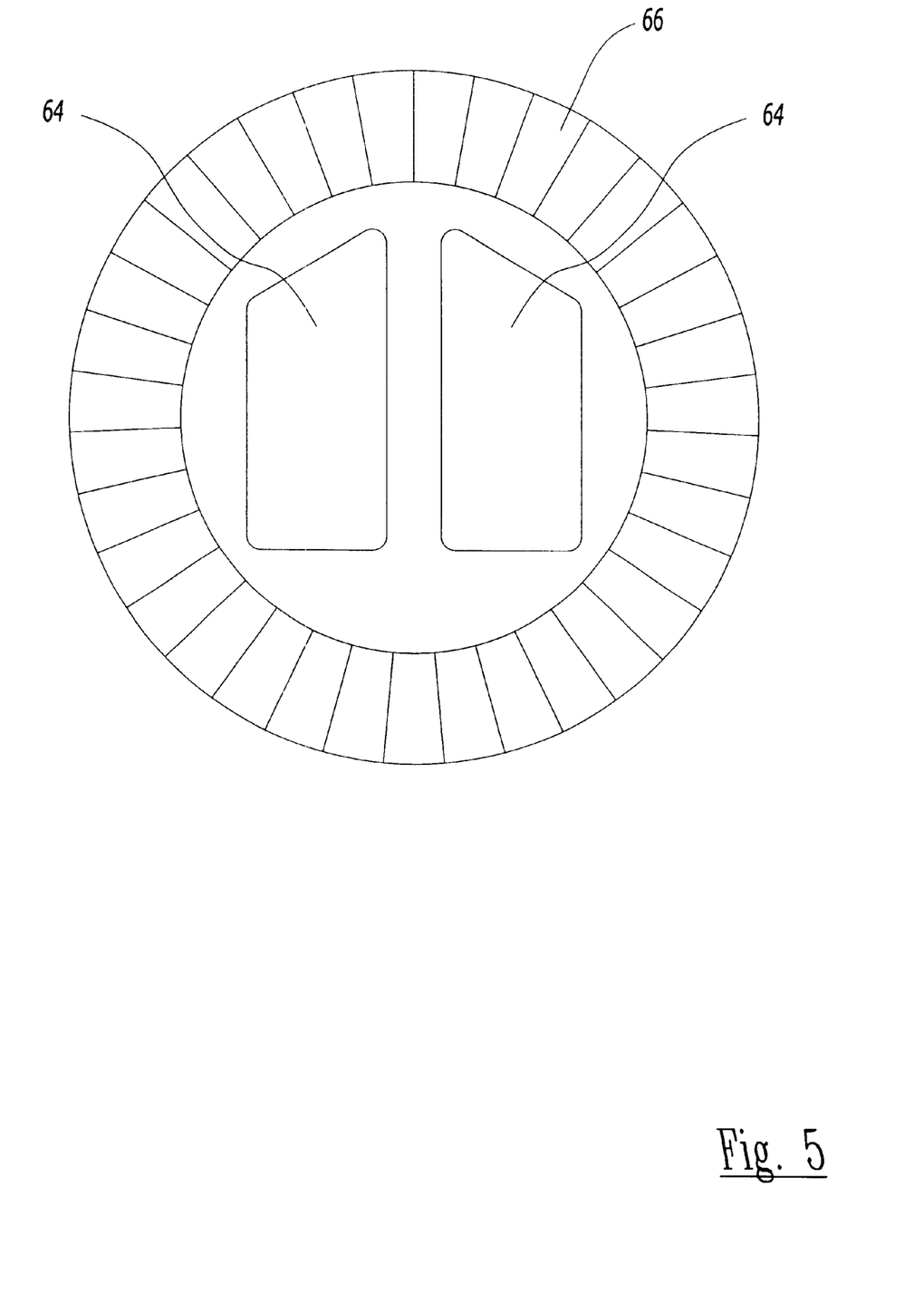
FIG. 5 is a bottom plan view of one embodiment of the ECG electrode and transmitter.

FIG. 5 shows a bottom view of the electrode and transmitter 42. Electrode 42 has a sensor 64. Sensor 64 is a conventional ECG electrical sensor. Electrode 42 also has an adhesive strip 66 attached to the bottom. The adhesive strip 66 is in a relationship to the sensor 64 such that sensor 64 rests flush against a patient's skin. Sensor 64 could be a thermistor or other sensor capable of monitoring human signals.

Figure 6:
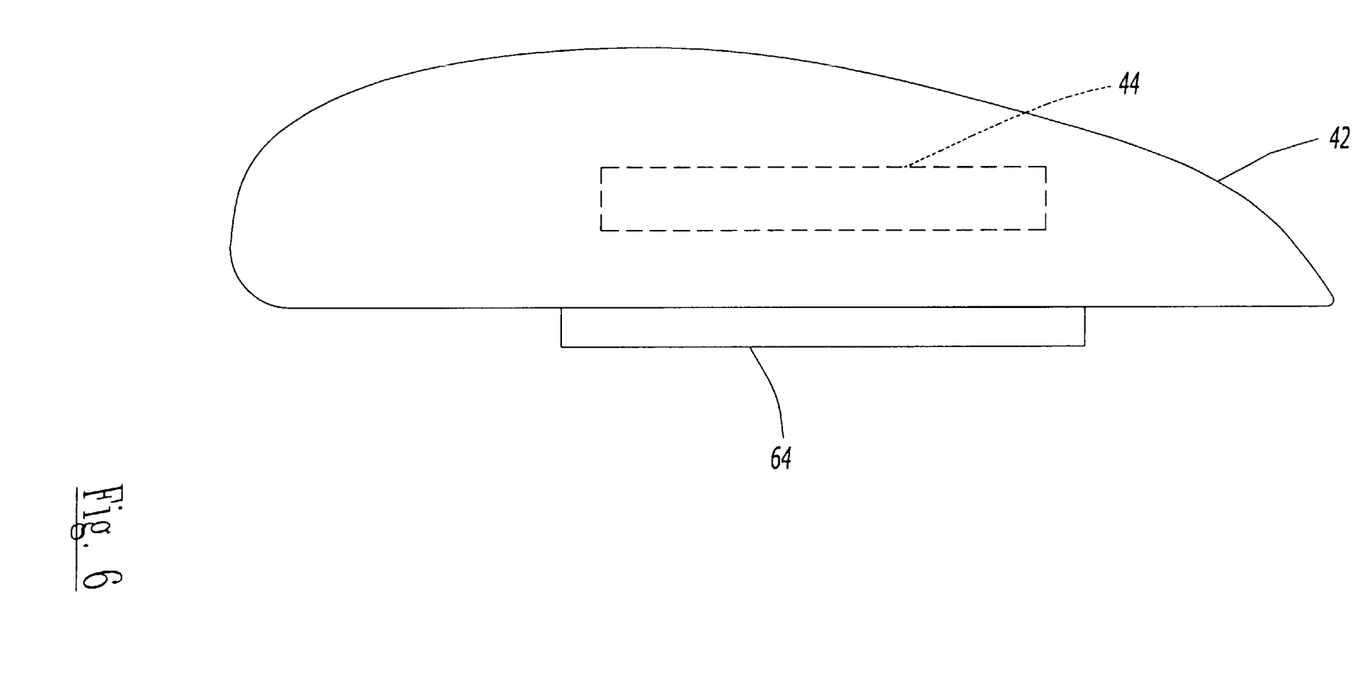
FIG. 6 is a side view of one embodiment of the ECG electrode and transmitter.

FIG. 6 is a side view of electrode 42. The embodiment shown in FIG. 6 has the adhesive strip 66 removed. Electrode 42 contains an internal antenna 44. Of course, the antenna 44 could be external. Preferably, antenna 42 is an omnidirectional antenna.

It should be pointed out that electrode 42 could also include a receiver, or could include a transceiver, rather than just a transmitter. In addition receiver 46 could be also be equipped with a transmitter. This configuration would facilitate two-way communication between the electrode 42 and the receiver 46. The receiver 46 with a transmitter could also be used for secondary transmissions to remote receivers, rather than for two-way communication with the electrode 42. The electrode 42 could have a receiver and receive signals from a transmitter which is operatively connected to a computer, rather than from a transmitter coupled with the receiver 46. A transmitter connected to a computer could output a signal which "instructs" electrode 42 to perform a certain function, such as begin transmission, or turn the power off.

Note that rather than sensing a heart biopotential, other biopotentials could be sensed. For example, electromyograms, electroencephalograms, oxygen saturation, pulse rates, blood pressures, or body temperature could be sensed and transmitted to a remote receiver. The present invention is intended to cover these applications, as well as other situations not specifically mentioned herein.

A general description of the present invention as well as preferred embodiment has been set forth about. Those skilled in the art will recognize and will be able to practice additional variations and the methods and devices described which fall within the teachings of this invention. Accordingly, all such modifications and additions are deemed to be within the scope of the invention which is to be limited only by the claims appended hereto.

I claim:

1. A wireless biopotential monitoring device which has the advantages of limiting electromagnetic interference and consuming low power, comprising:

a housing;

a biopotential sensor for positioning externally on a body, the biopotential sensor operatively attached to the housing;

a first transmitter in operative communication with the sensor and operatively attached to the housing, the transmitter adapted to broadcast a first signal which is modulated by the sensed biopotential;

wherein the first transmitter is further adapted to limit the power of the first signal so that the first signal will attenuate to at most a negligible value within a predetermined distance from the transmitter;

the transmitter is further adapted to place information on the broadcast signal which identifies a location where the biopotential sensor is attached; and a display operatively connected to the biopotential sensor and secured to the housing.

2. The biopotential monitoring system of claim 1, wherein the predetermined distance is fifteen feet.

3. The biopotential monitoring system of claim 1, wherein the predetermined distance is ten feet.

4. The biopotential monitoring system of claim 1, further comprising:

a first receiver which is adapted to receive the first signal.

5. The biopotential monitoring system of claim 4, further comprising:

a computer in operative communication with the first receiver.

6. The biopotential monitoring system of claim 5, further comprising:

a second transmitter in operative communication with the computer, wherein the second transmitter is adapted to broadcast a second signal which contains instructions from the computer;

and a second receiver in operative communication with the biopotential sensor, the second receiver adapted to receive the second signal and adapted to instruct the sensor to perform a function based on the instructions.

7. The biopotential monitoring system of claim 6, wherein the function is turning the power off.

8. The biopotential monitoring system of claim 6, wherein the function is transmitting the first signal.

9. The biopotential monitoring system of claim 4, further comprising:

a second transmitter in operative communication with the first receiver, wherein the second transmitter is adapted to broadcast a second signal which contains instructions;

and a second receiver in operative communication with the biopotential sensor, the second receiver adapted to receive the second signal and adapted to instruct the sensor to perform a function based on the instructions.

10. The biopotential monitoring system of claim 1, wherein the biopotential sensor is an electrocardiogram sensor.

11. The biopotential monitoring system of claim 1, wherein the biopotential sensor is an electroencephalogram sensor.

12. The biopotential monitoring system of claim 1, wherein the biopotential sensor is an electromyogram sensor.

13. The biopotential monitoring system of claim 1, wherein the biopotential sensor is a thermistor.

14. The biopotential monitoring system of claim 1, wherein the biopotential sensor is a pulse oximeter.

15. A new method of monitoring a biopotential signal which has the advantages of limiting electromagnetic interference and consuming low power, comprising:

sensing a biopotential with an external biopotential sensor operatively attached to a housing;

displaying a location of the biopotential being sensed on a display operatively connected to the biopotential sensor and secured to the housing;

broadcasting a first signal from a first transmitter, the first signal being modulated by the sensed biopotential; and limiting the power of the first signal so that the first signal attenuates to at most a negligible value within a predetermined distance from a transmission point.

16. The method of claim 15, wherein the predetermined distance is fifteen feet.

17. The method of claim 15, wherein the predetermined distance is ten feet.

18. The method of claim 15, further comprising: utilizing a first receiver to receive the first signal.

19. The method of claim 18, further comprising:
communicating a signal from the first receiver to a computer, the signal from the receiver to the computer being dependent upon the received first signal.

20. The method of claim 15, wherein the sensed biopotential is a heart biopotential.

21. The method of claim 15, wherein the sensed biopotential is a muscle biopotential.

22. The method of claim 15, wherein the sensed biopotential is a brain biopotential.

23. The method of claim 15, wherein the sensed biopotential is oxygen saturation of blood.

24. The method of claim 15, further comprising:
transmitting a second signal from a second transmitter;
receiving the second signal at a second receiver;
performing a function with either the biopotential sensor or the first transmitter based on the second signal.

25. The method of claim 24, wherein the function is turning the power off.

26. The method of claim 24, wherein the function is starting or stopping transmitting the first signal.

* * * * *